(12) United States Patent
Farage

(10) Patent No.: US 7,137,970 B1
(45) Date of Patent: Nov. 21, 2006

(54) TEST METHOD FOR ASSESSING IRRITATION OF SKIN

(75) Inventor: Miranda Aref Farage, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/337,900

(22) Filed: Jan. 23, 2006

(51) Int. Cl.
A61M 35/00 (2006.01)
A61B 5/00 (2006.01)

(52) U.S. Cl. .................... 604/289; 604/290; 424/9.8
(58) Field of Classification Search ............... 604/289, 604/290; 424/400–405, 70.1–70.4, 9.8, 443; 514/27, 18; 601/17
See application file for complete search history.

(56) References Cited

U.S. PATENT DOCUMENTS

2004/0003670 A1* 1/2004 Minerath et al. .......... 73/865.7

FOREIGN PATENT DOCUMENTS

EP A 637616 2/1995

OTHER PUBLICATIONS

Serup, "A Three-hour Test for Rapid Comparison of Effects of Moisturizers and Active Constituents (Urea), Measurements of hydration, sealing and skin surface lipidization by noninvasive techniques", *Acta Derm Venereol*, Suppl. 177, pp. 29-33 (1992).

Jemec, et al., "Hydration and Placticity Following Long-term Use of a Moisturizer: A Single-blind Study", *Acta Derm Venereol*, vol. 82, pp. 322-324 (2002).

Tupker, et al., "Guidelines on sodium lauryl sulfate (SLS) exposure tests, A report from the Standardization Group* of the European Society of Contact Dermatitis", *Contact Dermatitis*, vol. 37, pp. 53-69 (1997).

Blanken, et al., "Effect of mineral oil and linoleic-acid-containing emulsions on the skin vapour loss of sodium-lauryl-sulphate-induced irritant skin reactions", *Contact Dermatitis*, vol. 20, pp. 93-97 (1989).

De Paepe, et al., "Claim substantiation and efficiency of hydrating body lotions and protective creams", *Contact Dermatitis*, vol. 42, pp. 227-234 (2000).

Zhai, et al., "A bioengineering study on the efficacy of a skin protectant lotion in preventing SLS-induced dermatitis", *Skin Research and Technology*, vol. 6, pp. 77-80 (2000).

Lukacovic, et al., "Forearm wash test to evaluate the clinical mildness of cleansing products", *J. Soc. Cosmet Chem.*, vol. 39, pp. 355-366 (Nov./Dec. 1988).

Ertel, et al., "A forearm controlled application technique for estimating the relative mildness of personal cleansing products", *J. Soc. Cosmet Chem.*, vol. 46, pp. 67-76 (Mar./Apr. 1995).

(Continued)

Primary Examiner—Jacqueline F. Stephens
(74) Attorney, Agent, or Firm—C. Brant Cook; Betty J. Zea; David M. Weirich

(57) ABSTRACT

Test methods for assessing irritation of portions of skin and/or assessing inhibition and/or reduction of such irritation are provided.

17 Claims, 3 Drawing Sheets

OTHER PUBLICATIONS

Farage, "Assessing the Skin Irritation Potential of Facial Tissues", *Cutaneous and Ocular Toxicology*, vol. 24, pp. 125-135 (2005).

Held, et al., "Effect of Different Moisturizers on SLS-Irritated Human Skin", *Contact Dermatitis*, vol. 44, pp. 229-234 (2001).

Held, et al., "Effect of Moisturizers on Skin Susceptibility to Irritants", *Acta Derm Venereol*, vol. 81, pp. 104-107 (2001).

Farage, "Development of a Modified Forearm Controlled Application Test Method for Evaluating the Skin Mildness of Disposable Wipe Products", *J. Cosmet. Sci.*, vol. 51, pp. 153-167 (May/Jun. 2000).

* cited by examiner

US 7,137,970 B1

TEST METHOD FOR ASSESSING IRRITATION OF SKIN

FIELD OF THE INVENTION

The present invention relates to test methods for assessing irritation of portions of skin and/or assessing inhibition and/or reduction of such irritation. More particularly, the present invention relates to test methods for assessing the inhibition and/or reduction of irritation of skin from fibrous structures, especially lotion-containing fibrous structures that come in contact with such irritated skin.

BACKGROUND OF THE INVENTION

Cold and allergy sufferers often develop irritation around the nostrils as a result of repeated and frequent rubbing of the skin site with facial tissues. This irritation is a combination of the inherent irritant properties of the tissue components (chemical irritation), and mechanical irritation from friction.

Over the years, formulators have tried to assess the irritation and/or the inhibition and/or reduction of such irritation by various products, such as topical lotions and creams.

A prior art test method comprised compromising a portion of skin with a chemical irritant and then directly applying a lotion to the irritated portion of skin.

Another prior art test method comprised compromising a portion of skin by tape stripping the portion of skin and then contacting the irritated portion of skin with a facial tissue in a one-wipe pass over the irritated portion of skin.

However, none of the existing prior art test methods are suitable for assessing skin irritation of cold sufferers because the irritation around one's nostrils during a cold is a combination of effects, including the inherent irritant properties of the tissue components (i.e., chemical irritants), and mechanical irritation from friction resulting from frequent and repeated rubbing of the irritated skin with a tissue.

Accordingly, there is a need for a test method that is capable of assessing the skin irritation present on the skin of a cold sufferer.

SUMMARY OF THE INVENTION

The present invention fulfills the need identified above by providing a test method that is capable of assessing irritation of portions of skin and/or assessing inhibition and/or reduction of such irritation.

In one example of the present invention, a method for assessing irritation of skin, the method comprising the steps of:
 a. irritating a portion of skin by a first mode;
 b. irritating the portion of skin by a second mode different from the first mode, wherein the second mode comprises rubbing a substrate on the portion of skin; and
 c. assessing erythema and/or dryness of the portion of the skin; and
 d. optionally, assessing objective instrumental measurements, is provided.

In another example of the present invention, a method for assessing irritation of skin, the method comprising the steps of:
 a. irritating a portion of skin by a first mode comprising contact the portion of skin with a chemical irritant;
 b. irritating the portion of skin by a second mode different from the first mode; and
 c. assessing erythema and/or dryness of the portion of the skin; and
 d. optionally, assessing objective instrumental measurements, is provided.

Accordingly, the present invention provides a test method that is capable of assessing irritation of portions of skin and/or assessing inhibition and/or reduction of such irritation.

DETAILED DESCRIPTION OF THE INVENTION

Definitions

Figure 1A:
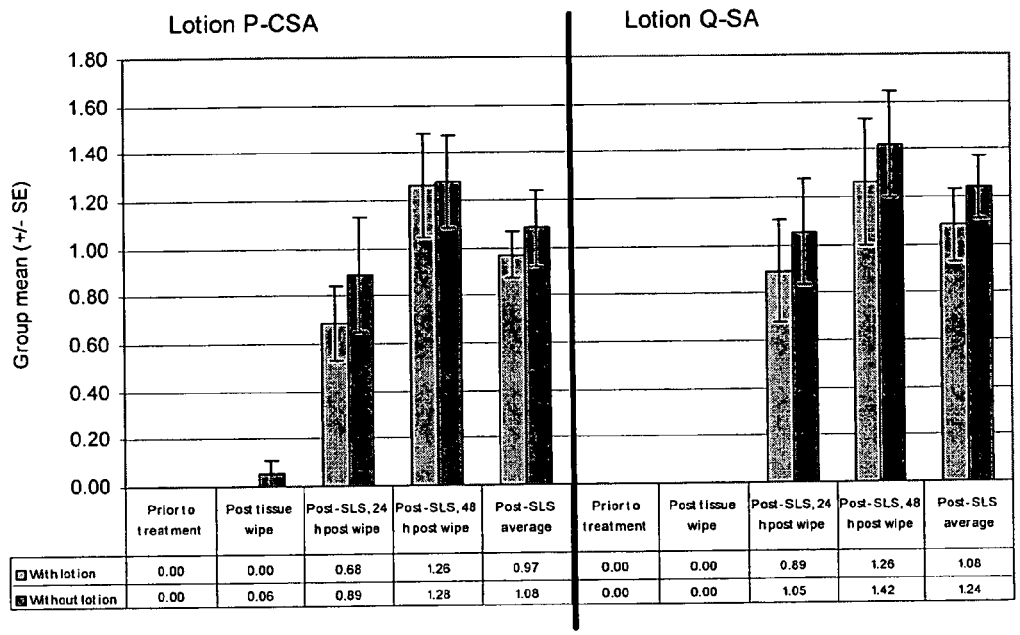
FIG. 1A is a bar chart showing dryness data from two substrates tested according to one example of the present invention.

"Mode" as used herein means a specific way of doing something. In the present case, it is a specific way out of numerous ways of irritating a portion of skin.

"Irritation" or "irritate" or "irritating" as used herein means that a portion of skin exhibits signs of chafing and/or inflammation and/or abrasion.

"Chemical irritation" as used herein means that a chemical agent contacts a portion of skin such that it irritates the portion of skin.

"Physical irritation" as used herein means that a non-chemical agent contacts a portion of skin in such a way to cause irritation of the portion of skin. Nonlimiting examples of sources of physical irritation include tape stripping the portion of skin, rubbing a substrate across the portion of skin, rubbing a hand across the portion of skin, occluding the skin from an external environment, and subjecting the portion of skin to excessive wind.

"Mechanical irritation" as used herein means a physical irritation that is caused by a physical object contacting the portion of skin to cause irritation.

"Frictional irritation" as used herein means a mechanical irritation that is caused by a physical object, such as a substrate, repeatedly contacting the portion of skin in a rubbing manner to cause irritation.

"Substrate" as used herein means a physical object upon which and/or within which one or more additive ingredients may be deposited.

"Fibrous structure" as used herein means a substrate that comprises one or more fibers, natural and/or synthetic. Nonlimiting examples of fibrous structures include feminine care products (pads, tampons, wipes), adult incontinence products, sanitary tissue products (facial tissue, toilet tissue, paper towels, wipes), baby care products (diapers, wipes), fabrics and home care products (cleaning wipes, dusting wipes).

"Sanitary tissue products" as used herein means facial tissue, toilet tissue, paper towels and wipes.

"Erythema" as used herein means visually recognizable redness of the skin.

"Dryness" as used herein means visually recognizable powderiness or cracking of the skin.

Test Method

The test method of the present invention comprises a method for assessing irritation of skin.

The method comprises the steps of:
a. irritating a portion of skin by a first mode;
b. irritating the portion of skin by a second mode different from the first mode, wherein the second mode comprises rubbing a substrate on the portion of skin; and
c. assessing erythema and/or dryness of the portion of the skin; and
d. assessing objective instrumental measurements.

The step of irritating a portion of skin may comprise chemically irritating a portion of skin and/or physically irritating a portion of skin.

Nonlimiting examples of portions of skin suitable for use in the present invention include forearm skin. In one example, the portion of skin is the volar and/or flexor surface portion of the forearm. Two, three or more portions of skin on one forearm may be subjected to the test method of the present invention. The portions of skin may be any size. In one example, the size of the portion of skin is 4 cm×4 cm. Portions of skin may be 4 cm apart from the other on the forearm.

A nonlimiting example of chemical irritation of a portion of skin includes contacting the portion of skin with a skin irritant agent. Nonlimiting examples of suitable skin irritants include sodium lauryl sulfate and sodium laureth sulfate.

A nonlimiting example of physical irritation of a portion of skin includes tape stripping the portion of skin. In other words, applying a piece of tape to the portion of skin and then removing the tape such that the portion of skin becomes irritated.

Another nonlimiting example of physical irritation of a portion of skin includes occluding the portion of skin. One way of occluding comprises placing a patch, such as a Webril® patch, commercially available from Professional Medical Products Company) over the portion of skin. Tape, such as an occlusive, hypoallergenic tape, such as Blenderm® tape, commercially available from 3M Company, may be used to cover the patch and hold the patch in place on the portion of skin. The patch may also comprise a skin irritant to facilitate irritation of the skin.

The rubbing of the substrate across the portion of skin can occur in a back and forth manner, a circular manner and/or a multi-directional (two or more) manner and/or in a unidirectional manner, if the skin has been chemically irritated prior to rubbing.

The substrate may be a fibrous structure.

The fibrous structure may be embossed and/or may be pattern-densified.

The fibrous structure may be creped or uncreped.

The fibrous structure may comprise a nonwoven web.

The fibrous structure may comprise a cellulosic fiber containing web.

In one example, the substrate is a single- or multi-ply sanitary tissue product, specifically a sanitary tissue product comprising an additive ingredient, such as a lotion.

The additive ingredient may be present on a surface of the substrate. When the additive ingredient is a lotion and it is present on the surface of the substrate, a silicone may be present directly on the substrate and then the lotion may be present on top of the silicone. The lotion may be a transferable lotion, a minimally transferable lotion or a non-transferable lotion.

Nonlimiting examples of additive ingredients include chemical softening agents, dyes, colorants, surfactants, absorbents, permanent wet strength agents, temporary wet strength agents, antiviral agents, oils, nanotechnology agents, lotion compositions, skin benefits agents, skin healants, perfumes, especially long lasting and/or enduring perfumes, antibacterial agents, botanical agents, disinfectants, pharmaceutical agents, film formers, deodorants, opacifiers, astringents, solvents, cooling sensate agents such as camphor, thymol and menthol, and preservatives.

Nonlimiting examples of suitable chemical softening agents include silicones, quaternary ammonium compounds, petrolatum, oils, and mixtures thereof.

Nonlimiting examples of silicones include aminosilicones and/or cationic silicones.

In another example of the present invention, the method comprises the steps of:
a. irritating a portion of skin by a first mode comprising contact the portion of skin with a chemical irritant;
b. irritating the portion of skin by a second mode different from the first mode;
c. assessing erythema and/or dryness of the portion of the skin; and
d. assessing objective instrumental measurements.

The methods of the present invention may include pretreatment steps prior to irritating a portion of skin. Nonlimiting examples of pretreatment steps include contacting a portion of skin with an additive ingredient, such as a lotion.

Assessing erythema and/or dryness of the portion of the skin can be done visually. For example, a panel of experts can visually grade erythema and/or dryness of a portion of skin. Suitable grading scales for both erythema and dryness are set out below in Tables 1 and 2, respectively.

TABLE 1

Erythema Grading Scale

| | |
|---|---|
| 0 | No apparent cutaneous involvement |
| 0.5 | Faint, barely perceptible erythema or slight dryness |
| 1 | Faint, but definite erythema, definite dryness |
| 1.5 | Well-defined erythema or faint erythema with definite dryness |
| 2 | Moderate erythema; may have papules or deep fissures |
| 2.5 | Moderate erythema with barely perceptible edema; may have a few papules |
| 3 | Severe erythema (beet redness); may have generalized papules |
| 3.5 | Moderate-to-severe erythema with moderate edema |
| 4 | Moderate-to-severed erythema and/or extending edema, may have generalized vesicles or eschar formations |

TABLE 2

Dryness Grading Scale

| | |
|---|---|
| 0 | None |
| 1 | Patchy, slight powderiness with small scales |
| 2 | General, slight powderiness with small lifting scales |
| 3 | General, moderate powderiness with cracking and scales |
| 4 | General, heavy powderiness with cracking and lifting scales |
| 5 | Heavy cracking (possibly bleeding) and lifting scales |
| 6 | Severe cracking, with bleeding and sloughing of large scales |

The step of assessing erythema and/or dryness by objective instrumental measurements may include evaluating the portion of skin with a transepidermal water loss instrument, commercially available from Cortex Technology, Denmark under the tradename TEWL, DermaLab® Evaporimeter. Participants may be conditioned in a temperature and humidity controlled room (73° F.±4° F. (about 23° C.±2.2° C.) and a relative humidity of 50%±10%) for approximately 20 minutes.

Even though the description above of this test method is directed to assessing irritation of skin, one can also measure lotion or additive (such as perfumes, preservatives, antiviral, antibacterial, skin healants, skin benefit agents, non-active agents) transfer during this test method by determining the amount of lotion or other additive that transfers from the substrate to the skin.

Additive Ingredients

Nonlimiting examples of additive ingredients that may be incorporated on and/or in the substrate include surface treating compositions including, but not limited to, nanotechnology agents, lotion compositions, skin benefit agents, perfumes, especially long lasting and/or enduring perfumes, antibacterial agents, antiviral agents, botanical agents, disinfectants, pharmaceutical agents, film formers, deodorants, opacifiers, astringents, solvents, cooling sensate agents, such as camphor, thymol and menthol.

A surface treating composition, for purposes of the present invention, is a composition that improves the tactile sensation of a surface of a substrate, such as a fibrous structure, perceived by a user whom holds the substrate and rubs it across the user's skin. Such tactile perceivable softness can be characterized by, but is not limited to, friction, flexibility, and smoothness, as well as subjective descriptors, such as a feeling like lubricious, velvet, silk or flannel.

The surface treating composition may or may not be transferable. Typically, it is substantially non-transferable.

The surface treating composition may increase or decrease the surface friction of the surface of the fibrous structure, especially the user contacting surface of the fibrous structure. Typically, the surface treating composition will reduce the surface friction of the surface of the fibrous structure compared to a surface of the fibrous structure without such surface treating composition.

Nonlimiting examples of suitable surface treating agents can be selected from the group consisting of: polymers such as polyethylene and derivatives thereof, hydrocarbons, waxes, oils, silicones, organosilicones (oil compatible), quaternary ammonium compounds, fluorocarbons, substituted $C_{10}$–$C_{22}$ alkanes, substituted $C_{10}$–$C_{22}$ alkenes, in particular derivatives of fatty alcohols and fatty acids (such as fatty acid amides, fatty acid condensates and fatty alcohol condensates), polyols, derivatives of polyols (such as esters and ethers), sugar derivatives (such as ethers and esters), polyglycols (such as polyethyleneglycol) and mixtures thereof.

In one example, the surface treating composition of the present invention is a microemulsion and/or a macroemulsion of a surface treating agent (for example an aminofunctional polydimethylsiloxane, specifically an aminoethylaminopropyl polydimethylsiloxane) in water. In such an example, the concentration of the surface treating agent within the surface treating composition may be from about 3% to about 60% and/or from about 4% to about 50% and/or from about 5% to about 40%. A nonlimiting examples of such microemulsions are commercially available from Wacker Chemie (MR1003, MR103, MR102). A nonlimiting example of such a macroemulsion is commercially available from General Electric Silicones (CM849).

Nonlimiting examples of suitable waxes may be selected from the group consisting of: paraffin, polyethylene waxes, beeswax and mixtures thereof.

Nonlimiting examples of suitable oils may be selected from the group consisting of: mineral oil, silicone oil, silicone gels, petrolatum and mixtures thereof.

Nonlimiting examples of suitable silicones may be selected from the group consisting of: polydimethylsiloxanes, aminosilicones, cationic silicones, quaternary silicones, silicone betaines and mixtures thereof.

Nonlimiting examples of quaternary ammonium compounds suitable for use in the present invention include the well-known dialkyldimethylammonium salts such as ditallowdimethylammonium chloride, ditallowdimethylammonium methylsulfate, di(hydrogenated tallow)dimethylammonium chloride. In one example, the surface treating composition comprises di(hydrogenated tallow)dimethylammonium chloride, commercially available from Witco Chemical Company Inc. of Dublin, Ohio as Varisoft 137®.

Nonlimiting examples of ester-functional quaternary ammonium compounds having the structures named above and suitable for use in the present invention include the well-known diester dialkyl dimethyl ammonium salts such as diester ditallow dimethyl ammonium chloride, monoester ditallow dimethyl ammonium chloride, diester ditallow dimethyl ammonium methyl sulfate, diester di(hydrogenated) tallow dimethyl ammonium methyl sulfate, diester di(hydrogenated)tallow dimethyl ammonium chloride, and mixtures thereof. In one example, the surface treating composition comprises diester ditallow dimethyl ammonium chloride and/or diester di(hydrogenated)tallow dimethyl ammonium chloride, both commercially available from Witco Chemical Company Inc. of Dublin, Ohio under the tradename "ADOGEN SDMC".

For purposes herein, nanotechnology agents are defined as particles exhibiting average diameters of about 500 nm or less. In one example, particle size distributions of the nanotechnology agents in the present invention may fall anywhere within the range from about 2 nm to less than about 500 nm, alternatively from about 2 nm to less than about 100 nm, and alternatively from about 2 nm to less than about 50 nm. For example, a layer synthetic silicate can have a mean particle size of about 25 nanometers while its particle size distribution can generally vary between about 10 nm to about 40 nm. Alternatively, nanotechnology agents can also include crystalline or amorphous particles with a particle size from about 2 to about 100 nanometers, alternatively from about 2 to about 50 nanometers.

Inorganic nanotechnology agents generally exist as oxides, silicates, carbonates and hydroxides. Some layered clay minerals and inorganic metal oxides can be examples of nanotechnology agents. The layered clay minerals suitable for use in the present invention include those in the geological classes of the smectites, the kaolins, the illites, the chlorites, the attapulgites and the mixed layer clays. Typical examples of specific clays belonging to these classes are the smectices, kaolins, illites, chlorites, attapulgites and mixed layer clays. Smectites, for example, include montmorillonite, bentonite, pyrophyllite, hectorite, saponite, sauconite, nontronite, talc, beidellite, volchonskoite and vermiculite. Kaolins include kaolinite, dickite, nacrite, antigorite, anauxite, halloysite, indellite and chrysotile. Illites include bravaisite, muscovite, paragonite, phlogopite and biotite. Chlorites include corrensite, penninite, donbassite, sudoite, pennine and clinochlore. Attapulgites include sepiolite and polygorskyte. Mixed layer clays include allevardite and vermiculitebiotite. Variants and isomorphic substitutions of these layered clay minerals offer unique applications.

The layered clay minerals of the present invention may be either naturally occurring or synthetic. Example of suitable nanotechnology agents include natural or synthetic hectorites, montmorillonites and bentonites. Other examples include hectorites clays. Commercially available, and typical sources of commercial hectorites are the LAPONITEs from Southern Clay Products, Inc., U.S.A; Veegum Pro and Veegum F from R. T. Vanderbilt, U.S.A.; and the Barasyms, Macaloids and Propaloids from Baroid Division, National Read Comp., U.S.A.

The inorganic metal oxides of the present invention may be silica- or alumina-based nanotechnology agents that are naturally occurring or synthetic. Aluminum can be found in many naturally occurring sources, such as kaolinite and bauxite. The naturally occurring sources of alumina are processed by the Hall process or the Bayer process to yield the desired alumina type required. Various forms of alumina are commercially available in the form of Gibbsite, Diaspore, and Boehmite from manufactures such as Condea, Inc.

Boehmite alumina is a water dispersible, inorganic metal oxide having a mean particle size distribution of about 25 nanometers. Such product is commercially available, for example under the trade name Disperal P2™.

Natural clay minerals typically exist as layered silicate minerals and less frequently as amorphous minerals. A layered silicate mineral has $SiO_4$ tetrahedral sheets arranged into a two-dimensional network structure. A 2:1 type layered silicate mineral has a laminated structure of several to several tens of silicate sheets having a three layered structure in which a magnesium octahedral sheet or an aluminum octahedral sheet is sandwiched between two sheets of silica tetrahedral sheets.

A sheet of an expandable layer silicate has a negative electric charge, and the electric charge is neutralized by the existence of alkali metal cations and/or alkaline earth metal cations. Smectite or expandable mica can be dispersed in water to form a sol with thixotropic properties. Further, a complex variant of the smectite type clay can be formed by the reaction with various cationic organic or inorganic compounds. As an example of such an organic complex, an organophilic clay in which a dimethyldioctadecyl ammonium ion(a quaternary ammonium ion) is introduced by cation exchange and has been industrially produced and used as a gellant of a coating.

With appropriate process control, the processes for the production of synthetic nanoscale powders (i.e. synthetic clays) does indeed yield primary particles, which are nanoscale. However, the particles are not usually present in the form of discrete particles, but instead predominantly assume the form of agglomerates due to consolidation of the primary particles. Such agglomerates may reach diameters of several thousand nanometers, such that the desired characteristics associated with the nanoscale nature of the particles cannot be achieved. The particles may be deagglomerated, for example, by grinding as described in EP-A 637,616 or by dispersion in a suitable carrier medium, such as water or water/alcohol and mixtures thereof.

The production of nanoscale powders such as layered hydrous silicate, layered hydrous aluminum silicate, fluorosilicate, mica-montmorillonite, hydrotalcite, lithium magnesium silicate and lithium magnesium fluorosilicate are common. An example of a substituted variant of lithium magnesium silicate is where the hydroxyl group is partially substituted with fluorine. Lithium and magnesium may also be partially substituted by aluminum. In fact, the lithium magnesium silicate may be isomorphically substituted by any member selected from the group consisting of magnesium, aluminum, lithium, iron, chromium, zinc and mixtures thereof.

Synthetic hectorite was first synthesized in the early 1960's and is now commercially marketed under the trade name LAPONITE™ by Southern Clay Products, Inc. There are many grades or variants and isomorphous substitutions of LAPONITE™ marketed. Examples of commercial hectorites are LAPONITE B™, LAPONITE S™, LAPONITE XLS™, LAPONITE RD™ and LAPONITE RDS™. One embodiment of this invention uses LAPONITE XLS™ having the following characteristics: analysis (dry basis) $SiO_2$ 59.8%, MgO 27.2%, $Na_2O$ 4.4%, $Li_2O$ 0.8%, structural $H_2O$ 7.8%, with the addition of tetrasodium pyrophosphate (6%); specific gravity 2.53; bulk density 1.0.

Synthetic hectorites, such as LAPONITE RD™, do not contain any fluorine. An isomorphous substitution of the hydroxyl group with fluorine will produce synthetic clays referred to as sodium magnesium lithium fluorosilicates. These sodium magnesium lithium fluorosilicates, marketed as LAPONITE™ and LAPONITE S™, may contain fluoride ions of up to approximately 10% by weight. It should be understood that the fluoride ion content useful in the compositions described herein can comprise any whole or decimal numeric percentage between 0 and 10 or more. LAPONITE B™, a sodium magnesium lithium fluorosilicate, has a flat, circular plate-like shape, and may have a diameter with a mean particle size, depending on fluoride ion content, that is any number (or narrower set of numbers) that is within the range of between about 25–100 nanometers. For example, in one non-limiting embodiment, LAPONITE B™ may be between about 25–40 nanometers in diameter and about 1 nanometer in thickness. Another variant, called LAPONITE S™, contains about 6% of tetrasodium pyrophosphate as an additive. In some instances, LAPONITE B™ by itself is believed, without wishing to be bound to any particular theory, to be capable of providing a more uniform coating (that is, more continuous, i.e., less openings in the way the coating forms after drying), and can provide a more substantive (or durable) coating than some of the other grades of LAPONITE™ by themselves (such as LAPONITE RD™). The coating preferably forms at least one layer of nanotechnology agents on the surface which has been coated, and is substantially uniform.

Inorganic metal oxides generally fall within two groups-photoactive and non-photoactive nanotechnology agents. General examples of photoactive metal oxide nanotechnology agents include zinc oxide and titanium oxide. Photoactive metal oxide nanotechnology agents require photoactivation from either visible light (e.g. zinc oxide) or from UV light ($TiO_2$). Zinc oxide coatings have generally been used as anti-microbial agents or as anti-fouling agents.

Non-photoactive metal oxide nanotechnology agents do not use UV or visible light to produce the desired effects. Examples of non-photoactive metal oxide nanotechnology agents include, but are not limited to: silica and alumina nanotechnology agents, and mixed metal oxide nanotechnology agents including, but not limited to smectites, saponites, and hydrotalcite.

A lotion composition may comprise oils and/or emollients and/or waxes and/or immobilizing agents.

The lotion compositions may be heterogeneous. They may contain solids, gel structures, polymeric material, a multiplicity of phases (such as oily and water phase) and/or emulsified components. It may be difficult to determine precisely the melting temperature of the lotion composition, i.e. difficult to determine the temperature of transition between the liquid form, the quasi-liquid from, the quasi-solid form and the solid form. The terms melting temperature, melting point, transition point and transition temperature are used interchangeably in this document and have the same meaning.

The lotion compositions may be semi-solid, of high viscosity so they do not substantially flow without activation during the life of the product or gel structures.

The lotion compositions may be shear thinning and/or they may strongly change their viscosity around skin temperature to allow for transfer and easy spreading on a user's skin.

The lotion compositions may be in the form of emulsions and/or dispersions.

A nonlimiting example of a suitable lotion composition of the present invention comprises a chemical softening agent, such as an emollient, that softens, soothes, supples, coats, lubricates, or moisturizes the skin. The lotion composition may sooth, moisturize, and/or lubricate a user's skin.

The lotion composition may comprise an oil and/or an emollient. Nonlimiting examples of suitable oils and/or emollients include glycols (such as propylene glycol and/or glycerine), polyglycols (such as triethylene glycol), petrolatum, fatty acids, fatty alcohols, fatty alcohol ethoxylates, fatty alcohol esters and fatty alcohol ethers, fatty acid ethoxylates, fatty acid amides and fatty acid esters, hydrocarbon oils (such as mineral oil), squalane, fluorinated emollients, silicone oil (such as dimethicone) and mixtures thereof.

Nonlimiting examples of emollients useful in the present invention can be petroleum-based, fatty acid ester type, alkyl ethoxylate type, or mixtures of these materials. Suitable petroleum-based emollients include those hydrocarbons, or mixtures of hydrocarbons, having chain lengths of from 16 to 32 carbon atoms. Petroleum based hydrocarbons having these chain lengths include petrolatum (also known as "mineral wax," "petroleum jelly" and "mineral jelly"). Petrolatum usually refers to more viscous mixtures of hydrocarbons having from 16 to 32 carbon atoms. A suitable Petrolatum is available from Witco, Corp., Greenwich, Conn. as White Protopet® 1 S.

Suitable fatty acid ester emollients include those derived from long chain $C_{12}$–$C_{28}$ fatty acids, such as $C_{16}$–$C_{22}$ saturated fatty acids, and short chain $C_1$–$C_8$ monohydric alcohols, such as $C_1$–$C_3$ monohydric alcohols. Nonlimiting examples of suitable fatty acid ester emollients include methyl palmitate, methyl stearate, isopropyl laurate, isopropyl myristate, isopropyl palmitate, and ethylhexyl palmitate. Suitable fatty acid ester emollients can also be derived from esters of longer chain fatty alcohols ($C_{12}$–$C_{28}$, such as $C_{12}$–$C_{16}$) and shorter chain fatty acids e.g., lactic acid, such as lauryl lactate and cetyl lactate.

Suitable fatty acid ester type emollients include those derived from $C_{12}$–$C_{28}$ fatty acids, such as $C_{16}$–$C_{22}$ saturated fatty acids, and short chain ($C_1$–$C_8$ and/or $C_1$–$C_3$) monohydric alcohols. Representative examples of such esters include methyl palmitate, methyl stearate, isopropyl laurate, isopropyl myristate, isopropyl palmitate, and ethylhexyl palmitate. Suitable fatty acid ester emollients can also be derived from esters of longer chain fatty alcohols ($C_{12}$–$C_{28}$ and/or $C_{12}$–$C_{16}$) and shorter chain fatty acids e.g., lactic acid, such as lauryl lactate and cetyl lactate.

Suitable alkyl ethoxylate type emollients include $C_{12}$–$C_{18}$ fatty alcohol ethoxylates having an average of from 3 to 30 oxyethylene units, such as from about 4 to about 23. Nonlimiting examples of such alkyl ethoxylates include laureth-3 (a lauryl ethoxylate having an average of 3 oxyethylene units), laureth-23 (a lauryl ethoxylate having an average of 23 oxyethylene units), ceteth-10 (acetyl ethoxylate having an average of 10 oxyethylene units), steareth-2 (a stearyl ethoxylate having an average of 2 oxyethylene units) and steareth-10 (a stearyl ethoxylate having an average of 10 oxyethylene units). These alkyl ethoxylate emollients are typically used in combination with the petroleum-based emollients, such as petrolatum, at a weight ratio of alkyl ethoxylate emollient to petroleum-based emollient of from about 1:1 to about 1:3, preferably from about 1:1.5 to about 1:2.5.

The lotion compositions of the present invention may include an "immobilizing agent", so-called because they are believed to act to prevent migration of the emollient so that it can remain primarily on the surface of the fibrous structure to which it is applied so that it may deliver maximum softening benefit as well as be available for transferability to the user's skin.

Immobilizing agents include agents that are may prevent migration of the emollient into the fibrous structure such that the emollient remain primarily on the surface of the fibrous structure and/or sanitary tissue product and/or on the surface treating composition on a surface of the fibrous structure and/or sanitary tissue product and facilitate transfer of the lotion composition to a user's skin. Immobilizing agents may function as viscosity increasing agents and/or gelling agents.

Nonlimiting examples of suitable immobilizing agents include waxes (such as ceresin wax, ozokerite, microcrystalline wax, petroleum waxes, fisher tropsh waxes, silicone waxes, paraffin waxes), fatty alcohols (such as cetyl, cetaryl, cetearyl and/or stearyl alcohol), fatty acids and their salts (such as metal salts of stearic acid), mono and polyhydroxy fatty acid esters, mono and polyhydroxy fatty acid amides, silica and silica derivatives, gelling agents, thickeners and mixtures thereof.

One or more skin benefit agents may be included in the substrate. Nonlimiting examples of skin benefit agents include zinc oxide, vitamins, such as Vitamin B3 and/or Vitamin E, sucrose esters of fatty acids, such as Sefose 1618S (commercially available from Procter & Gamble Chemicals), antiviral agents, anti-inflammatory compounds, lipid, inorganic anions, inorganic cations, protease inhibitors, sequestration agents, chamomile extracts, aloe vera, *calendula officinalis*, alpha bisalbolol, Vitamin E acetate and mixtures thereof.

Nonlimiting examples of suitable skin benefit agents include fats, fatty acids, fatty acid esters, fatty alcohols, triglycerides, phospholipids, mineral oils, essential oils, sterols, sterol esters, emollients, waxes, humectants and combinations thereof.

The skin benefit agent may be alone, included in a lotion composition and/or included in a surface treating composition. A commercially available lotion composition comprising a skin benefit agent is Vaseline® Intensive Care Lotion (Chesebrough-Pond's, Inc.).

Nonlimiting Example of Present Invention

Samples to be evaluated are obtained. Participants for the study are selected. Participants were excluded from the study if: 1) they were currently participating in any other clinical study, 2) they had participated in any type of research study involving the forearms within the previous twenty-one days, 3) they had allergies to soap, detergent, perfume, cosmetics, and/or toiletries, 4) they were taking anti-inflammatory corticosteriods or other medications that may interfere with test results, 5) they had had eczema or psoriasis within the past six months, 6) they had been diagnosed with skin cancer within the previous twelve months, 7) they were pregnant or lactating, or 8) they had cuts, scratches, rashes or any condition on their inner forearms that may prevent a clear assessment of their skin.

Participants are given an Olay® Sensitive Skin Care Bar for all bathing and showering needs to be used beginning with their enrollment into the study and until their participation in the study is complete. Instruct participants to avoid scrubbing the inner forearm areas and allow the soap and water to flow over the areas without washing. In addition, they are required to refrain from using lotions, creams, ointments, oils and/or moisturizers on the forearm areas.

Two to three test sites are identified and demarcated on each volar surface of the forearm. Test sites are measured 4 cm×4 cm, and were 4 cm apart. Each site is treated with a different sample. The samples are randomized, and the technician conducting the test is not aware of the test sample identity. Treatments at the test sites include a 24-h occluded patch of 0.3 ml of a solution of SLS, and wiping (rubbing) the test samples in a back and forth motion a specified number of times.

For the sample wipes, each sample is folded up to five times, and wiped 10 times in a back and forth movement (20 passes). The test sample is then refolded and the wiping repeated with a fresh area of the sample. New samples are used, as needed until the total number of back and forth wipes is completed. The SLS is patched using a Webril® patch (Professional Medical Products Company) covered by an occlusive, hypoallergenic tape (Blenderm®, 3M Company).

Scoring of the test sites is done at baseline (prior to any treatment) and before and after either patching with SLS or wiping with the test samples. When SLS patching is conducted, the patches are removed 30–60 minutes before grading. In all studies, visual scoring is conducted by expert graders under a 100 watt incandescent daylight bulb. If a test site exhibits an erythema grade of "2" or higher, that test site receives no further treatment.

EXAMPLES

Example 1

Facial Tissues Comprising Lotion

Figure 1B:
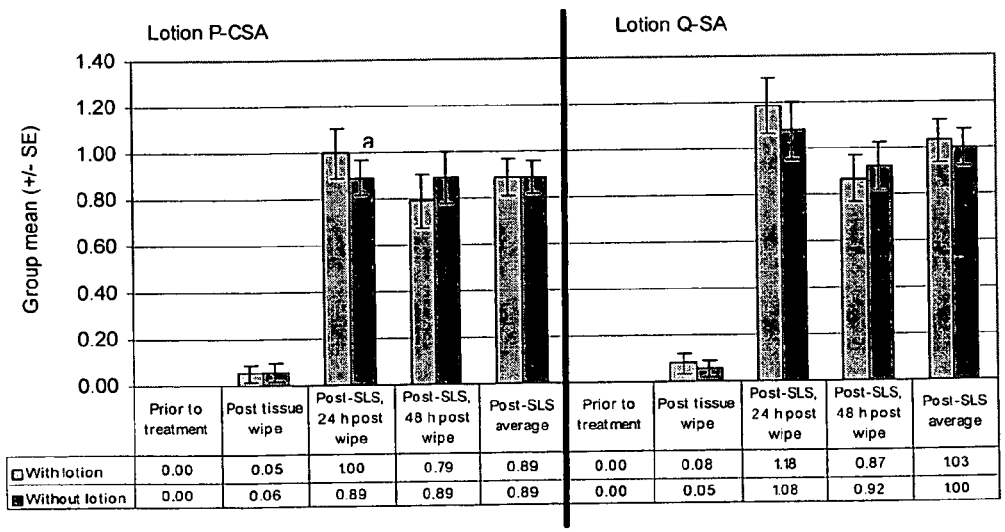
FIG. 1B is a bar chart showing erythema data from two substrates tested according to one example of the present invention.

Test sites on the flexor surfaces of the forearms of 19 subjects (participants) were wiped with the lotion-containing samples (tissues) on day 1 using a total of 200 wipes (400 passes) in order to pretreat the portion of skin with lotion. This was followed by a 24-h occlusive patch with 0.25% SLS (sodium lauryl sulfate). Visual scoring of erythema and dryness was conducted. Scoring of the test sites was done prior to any treatment, immediately after the sample wipes (post sample wipes), 30 minutes after removal of the SLS patch (post-SLS patch, 24-h post wipe), and 24 hours after removal of the SLS patch (post-SLS patch, 48-h post wipe). The group mean scores (+/−standard error) for dryness (a) and erythema (b) were determined for each scoring timepoint. Post-baseline average treatment comparisons were performed using analysis of variance ("ANOVA"). All other treatment comparisons were performed using the stratified Cochran Mantel Haenszel ("CMH") test. For Sample 1, the concentration of lotion on the sample was 0.668 mg/cm². Since Sample 2 is a currently marketed competitor's product, the lotion concentration is unknown. As shown in FIG. 1:

Sample 1 is statistically lower than tissue Sample 2 (with lotion) ($p<0.05$).

Example 2

Facial tissues comprising lotion

Figure 2A:
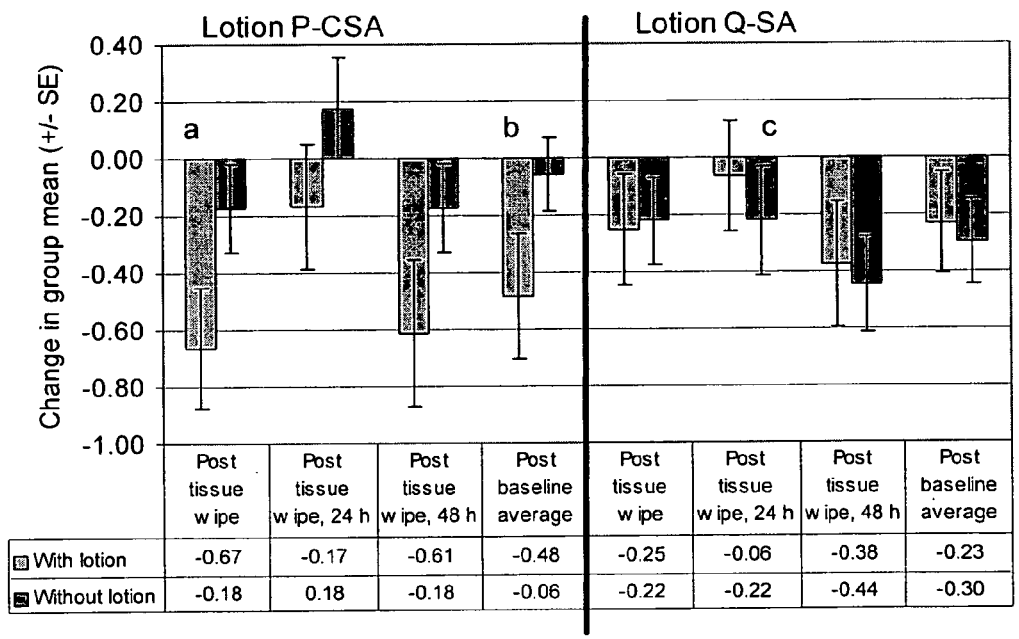
FIG. 2A is a bar chart showing dryness data from two substrates tested according to one example of the present invention.
Figure 2B:
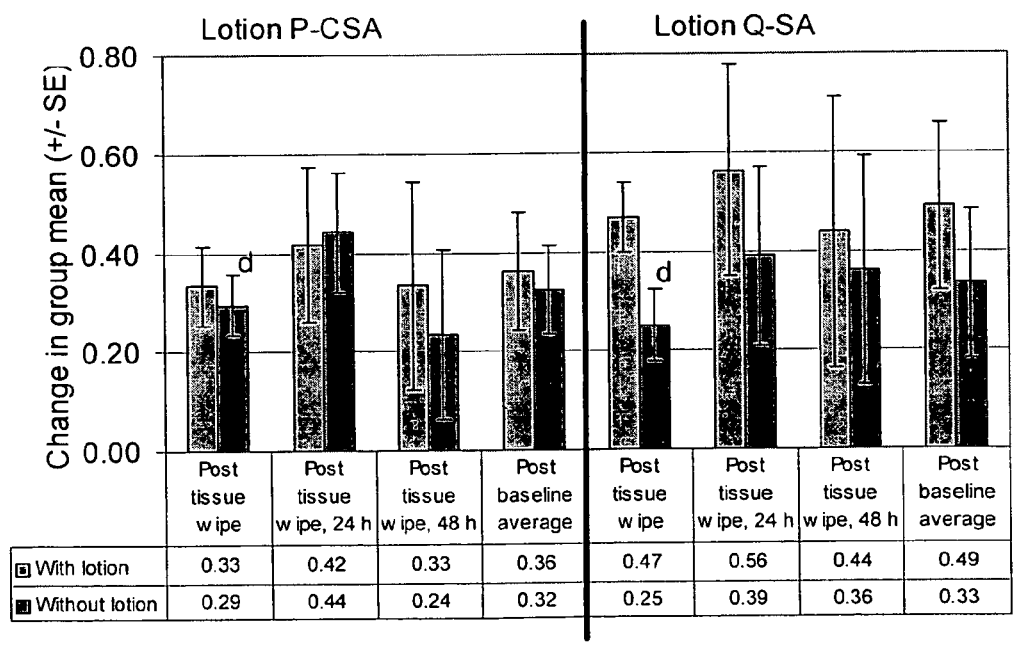
FIG. 2B is a bar chart showing erythema data from two substrates tested according to one example of the present invention.

Test sites on the flexor surfaces of the forearms of 18 subjects were pretreated by 24-h patch with 0.25% SLS. After patch removal, test sites were wiped with the test samples (tissues) using a total of 200 wipes (400 passes). Visual scoring of erythema and dryness of the test sites was done prior to any treatment, 30 minutes after removal of the SLS patch, immediately after the sample wipes (post sample wipe), and at 24 and 48 hours after the sample wipes (post-sample wipe, 24-h, and post-sample wipe, 48-h). The change from post-SLS baseline was determined for each subject, then the average over all subjects was calculated. The post-baseline average was calculated using the average of all post-baseline visits for each subject, then calculating the average over all subjects. Treatment comparisons for erythema at 24-h, 48-h, and the change in post-baseline average were performed using ANOVA on ranks. For Sample 1, the concentration of lotion was 0.668 mg/cm². Since Sample 2 is a currently marketed competitor's product, the lotion concentration is unknown. As shown in FIG. 2:

Sample 1 is statistically lower than Sample 2 (without lotion) ($p<0.05$).

Sample 2 is statistically lower than Sample 1 (without lotion) ($p<0.05$).

Sample 2 is statistically lower than Sample 1 (without lotion) ($p<0.05$).

Sample 1 is statistically lower than Sample 2 (with lotion) ($p<0.05$).

Example 3

Facial Tissues Comprising Lotion

Figure 3A:
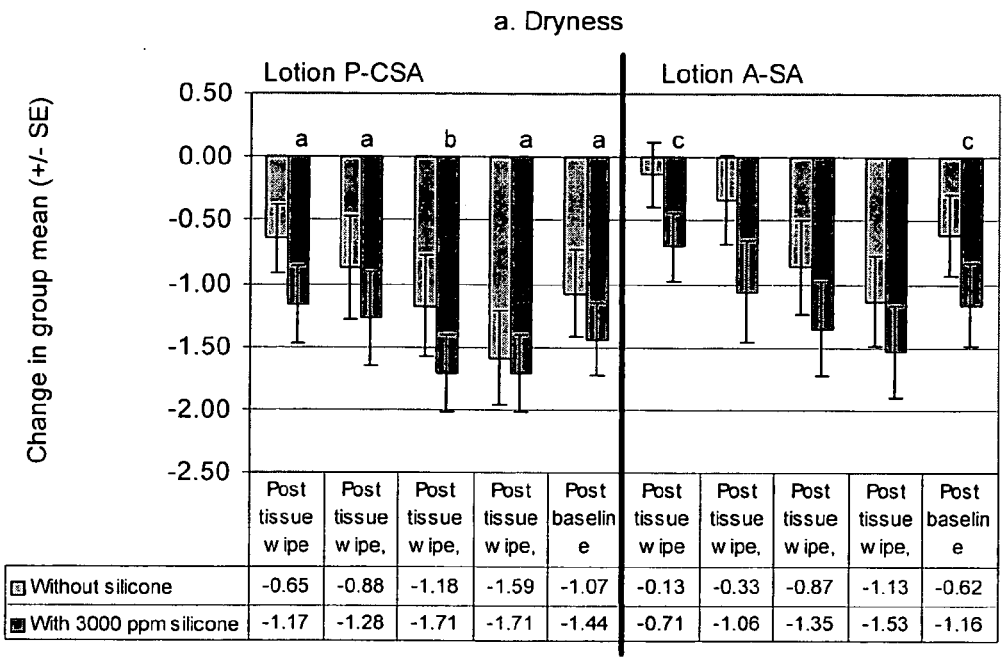
FIG. 3A is a bar chart showing dryness data from two substrates tested according to one example of the present invention.
Figure 3B:
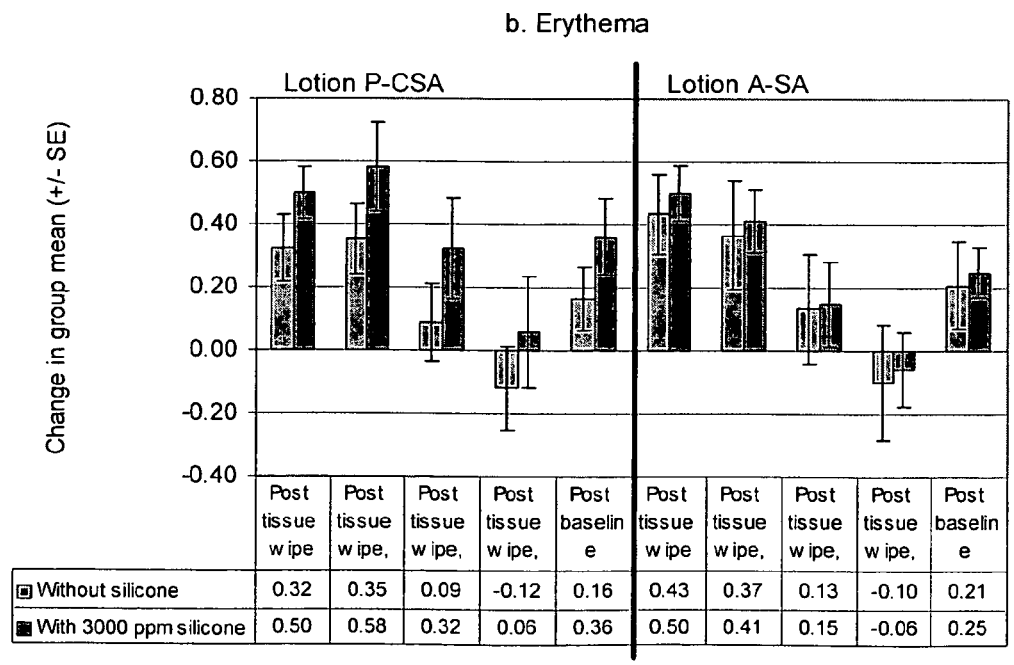
FIG. 3B is a bar chart showing erythema data from two substrates tested according to one example of the present invention.

Test sites on the flexor surfaces of the forearms of 15–18 subjects were pretreated by 24-h patch with 0.25% SLS. After patch removal, test sites were wiped with the test samples using a total of 200 wipes (400 passes). Visual scoring of erythema and dryness of the test sites was done prior to any treatment, 30 minutes after removal of the SLS patch, immediately after the sample wipes, and at 24, 48 and 72 hours after the sample wipes. The change from post-SLS baseline was determined for each subject, then the average over all subjects was calculated. The post-baseline average was calculated using the average of all post-baseline visits for each subject, then calculating the average over all subjects. Erythema post-baseline average comparisons were performed using ANOVA. All other treatment comparisons were performed using ANOVA on ranks. For Sample 1, the concentration of lotion was 0.668 mg/cm² and the concentration of lotion for Sample 2 was 0.815 mg/cm². Both samples had 3000 ppm of silicone on them. As shown in FIG. 3:

Sample 1 is statistically lower than Sample 2 (without silicone) ($p<0.05$).

Sample 1 is statistically lower than Sample 2 (without silicone) ($p<0.05$).

Sample 2 is statistically lower than tissue Sample 1 (without silicone) (p<0.05).

Example 4

Feminine Pads Comprising Lotion

Test sites on the flexor surfaces of the forearms of 19 subjects (participants) were wiped with the lotion-containing samples (feminine pads). On day 1 using a total of 120 wipes in order to pretreat the portion of skin with lotion. Different test products were used. This was followed by a 24-h occlusive patch with 0.25% SLS (sodium lauryl sulfate). Visual scoring of erythema and dryness was conducted. Scoring of the test sites was done prior to any treatment, immediately after the sample wipes (post sample wipes), 30 minutes after removal of the SLS patch (post-SLS patch, 24-h post wipe), and 24 hours after removal of the SLS patch (post-SLS patch, 48-h post wipe). The group mean scores (+/−standard error) for dryness (a) and erythema (b) were determined for each scoring timepoint. Objective instrumental measurements were taken using but not restricted to DermaLab® evaporimeter instrument will be used to assess transepidermal water loss (TEWL) at the test sites including the upper arm control site following all visual grading evaluations.

Post-baseline average treatment comparisons were performed using analysis of variance ("ANOVA"). All other treatment comparisons were performed using the stratified Cochran Mantel Haenszel ("CMH") test.

For all of Examples 1–3, the post-baseline average was calculated using the average of all post-baseline visits for each subject, then calculating the average over all subjects. If there were missing visits for a subject, that subject was not included in the calculation of the post-baseline average.

Additionally, in those experiments where SLS patching occurred prior to treatment with the lotion, the results are presented as the change in group mean. The change in group mean was calculated by determining the change from post-SLS baseline for each subject, then calculating the average over all subjects. In some cases, not all test subjects completed the entire test. In these instances, the scores recorded for the dropped subjects were removed from the calculation of the change in group mean for that timepoint.

All p-values were unadjusted for multiple comparisons.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assessing irritation of skin, the method comprising the steps of:
    a. irritating a portion of skin of a test subject by a first mode; and
    b. irritating the portion of skin by a second mode different from the first mode, wherein the second mode comprises rubbing a test sample substrate on the portion of skin;
    c. objectively assessing erythema and/or dryness of the portion of skin after the irritating steps.

2. The method according to claim 1 wherein the first mode is selected from the group consisting of: chemical irritation, physical irritation and mixtures thereof.

3. The method according to claim 2 wherein the first mode is chemical irritation.

4. The method according to claim 2 wherein the first mode is physical irritation.

5. The method according to claim 1 wherein the step of irritating a portion of skin by a first mode comprises contacting the portion of skin with a skin irritant agent.

6. The method according to claim 5 wherein the skin irritant agent is selected from the group consisting of: sodium lauryl sulfate, sodium laureth sulfate and mixtures thereof.

7. The method according to claim 1 wherein the step of irritating a portion of skin by a first mode comprises tape stripping the portion of skin.

8. The method according to claim 1 wherein the step of irritating a portion of skin by a first mode comprises occluding the portion of skin.

9. The method according to claim 1 wherein the substrate is a fibrous structure.

10. The method according to claim 9 wherein the fibrous structure is a sanitary tissue product.

11. The method according to claim 1 wherein the substrate comprises a fibrous structure comprising a lotion.

12. The method according to claim 1 wherein the substrate comprises an additive selected from the group consisting of: chemical softening agents, dyes, colorants, surfactants, absorbents, permanent wet strength agents, temporary wet strength agents, antiviral agents, oils, nanotechnology agents, lotion compositions, skin benefits agents, skin healants, perfumes, especially long lasting and/or enduring perfumes, antibacterial agents, botanical agents, disinfectants, pharmaceutical agents, film formers, deodorants, opacifiers, astringents, solvents, cooling sensate agents such as camphor, thymol and menthol, and preservatives.

13. The method according to claim 12 wherein the chemical softening agent is selected from the group consisting of: silicones, quaternary ammonium compounds, petrolatum, oils and mixtures thereof.

14. The method according to claim 13 wherein the silicones comprise aminosilicones.

15. The method according to claim 12 wherein the substrate comprises an antiviral agent.

16. The method according to claim 1 wherein the step of objectively assessing erythema and/or dryness comprises assessing erythema and/or dryness by an expert grader.

17. The method according to claim 1 wherein the step of objectively assessing erythema and/or dryness comprises assessing objective instrumental measurements of erythema and/or dryness.

* * * * *

UNITED STATES PATENT AND TRADEMARK OFFICE
CERTIFICATE OF CORRECTION

PATENT NO. : 7,137,970 B1  
APPLICATION NO. : 11/337900  
DATED : November 21, 2006  
INVENTOR(S) : Miranda Aref Farage It is certified that error appears in the above-identified patent and that said Letters Patent is hereby corrected as shown below:

Title Page

Line 1 of the second column, delete "sealing" and insert -- scaling --.

Column 4

(Line 54) (Line 10 of Table 1) delete "severed" and insert -- severe --.

Signed and Sealed this

Twenty-seventh Day of November, 2007

JON W. DUDAS  
*Director of the United States Patent and Trademark Office*